United States Patent
Kapral

[11] Patent Number: 5,980,873
[45] Date of Patent: Nov. 9, 1999

[54] ADDITIVE FOR COSMETICS AND OTHER TOPICALLY APPLIED MATERIALS

[76] Inventor: Ales M. Kapral, 12800 Reddington, Tucson, Ariz. 85749

[21] Appl. No.: 08/888,948

[22] Filed: Jul. 7, 1997

[51] Int. Cl.$^6$ .............................. A61K 7/043; A61K 7/00
[52] U.S. Cl. ................................. 424/61; 424/63; 424/64; 424/401; 424/673
[58] Field of Search .................................. 424/61, 63, 64, 424/401, 673

[56] References Cited

U.S. PATENT DOCUMENTS

| | | |
|---|---|---|
| 4,148,133 | 4/1979 | Kochel et al. . |
| 4,497,850 | 2/1985 | Umezono et al. . |
| 4,710,397 | 12/1987 | Yamazaki . |
| 4,959,425 | 9/1990 | Walker et al. . |
| 4,988,502 | 1/1991 | Ounanian et al. .......................... 424/63 |
| 5,063,997 | 11/1991 | Pachla et al. . |
| 5,100,839 | 3/1992 | Terao . |
| 5,221,423 | 6/1993 | Sugino et al. . |
| 5,394,425 | 2/1995 | Fukunaga et al. . |
| 5,501,733 | 3/1996 | Macaudiere et al. .................... 106/461 |
| 5,518,966 | 5/1996 | Woo . |
| 5,540,345 | 7/1996 | Sugimoto et al. . |
| 5,667,768 | 9/1997 | Ramin ........................................ 424/61 |
| 5,683,681 | 11/1997 | Ramin et al. .............................. 424/61 |

*Primary Examiner*—Sally Gardner-Lane

[57] ABSTRACT

A keratin composition which incorporates a metallic salt of fluoric acid increases the permeability of the user's skin allowing greater affect by the active agent. The affect of the salt of hydrofluoric acid is increased through the use of either water or alcohol mixed therewith. The composition so formed is useful for pharmaceutical treatments, topical cleansers, soaps, creams, and as additives to a variety of cosmetics.

22 Claims, 2 Drawing Sheets

ADDITIVE FOR COSMETICS AND OTHER TOPICALLY APPLIED MATERIALS

BACKGROUND OF THE INVENTION

This invention relates generally to the cosmetic field and more particularly to additives which assist in the permeability of the cosmetic.

A wide assortment of creams, cosmetics, soaps, and medicines are applied to the topical layer of the skin with the intended affect of addressing a condition of the skin. Some examples of treatments include conditions of dry skin and acne.

The effectiveness of the treatment is directly related to the permeability of the material to the user's skin. If the active ingredient is unable to reach beneath the skin, the affect of the active ingredient is, at best, limited.

One such active ingredient is keratin which is used for the treatment of a variety of skin conditions and is also incorporated into soaps and creams to improve the user's skin. Unfortunately, keratin does not readily permeate the skin layer, hence, the vast majority of the keratin applied is simply washed or worn off without having the desired affect.

It is clear there is a need for improved cosmetic permeability.

SUMMARY OF THE INVENTION

The invention provides a keratin composition which incorporates a metallic salt of fluoric acid to increase the permeability of the user's skin. With the user's skin more permeable, the keratin is able to be more fully absorbed and the curative affect of the keratin is maximized.

While the present discussion relates to keratin, those of ordinary skill in the art readily recognize that the invention is not so limited as other active ingredients are also contemplated. Keratin is the preferred active ingredient.

Products containing this invention's mixture increases the solubility or permeability of the keratin. This increased solubility is accomplished due to the nature of chemicals involved. While fluorides are typically stiff and brittle, they are softened significantly by the fluoric acid which also makes the keratin more soluble.

In many applications, the mixture of keratin with fluoric acid needs to be suspended so that the mixture does not precipitate. Suspension is accomplished by blending the mixture with a carboxyl or a gelatin. Those of ordinary skill in the art readily recognize a variety of other additives which can be used to properly suspend the mixture.

Once the mixture has been formed using a suspension mechanism (i.e. carboxyl), it more easily spread and can be applied to specific areas of the user's body without the keratin/fluoric acid spreading or running. One such application contemplated by this invention is the use of a suspended or gelatized mixture being applied to a user's nails to help harden the finger or toe nails. Another application contemplated is the use of gelatized mixture for the treatment of hair and also as an additive for cosmetics.

In some embodiments of the invention, the suspended or gelatized mixture of keratin/fluoric acid is applied to a paper sheet or other suitable substrate and packaged for single use application. In this manner, the user needs only open the package and spread the keratin/fluoric acid onto the affected area to obtain the desired treatment.

Keratin is any of various albuminoids characteristic of epidermal derivatives, such as nails and feathers, which are insoluble in protein solvents, have a high sulfur content, and generally contain cystine and arginine as the predominating amino acids.

Keratin has been shown to exhibit a wide variety of desirable pharmaceutical properties such as that described in U.S. Pat. No. 4,959,213, issued to Brod et al. on Sep. 25, 1990, and entitled "Pharmaceutical Composition for Treatment and/or prevention of diseases of the skin involving an Inflammatory Process", incorporated hereinto by reference. The Brod patent describes keratin's affect on erythema and acne.

Through the use of a metallic sale of fluoric acid, keratin becomes much more permeable.

Hydrofluoric acid is an aqueous solution of hydrogen fluoride (HF). The material is typically a colorless, fuming, poisonous liquid and is extremely corrosive. It is a weak acid compared to hydrochloric acid but will attack glass and other silica materials. It is often used to polish, frost, or etch glass and to pickle copper, brass, and alloy steels, to clean stone and brick and to acidize oil wells, and also to dissolve ores.

A salt is the reaction product when a metal displaces the hydrogen of an acid. As example, sodium fluoride (NaF) is formed by adding sodium carbonate to hydrofluoric acid.

The metallic salt of hydrofluoric acid, when combined with keratin, significantly increases the passage of the keratin through the skin so that the keratin has significantly more affect.

The action of the salt of hydrofluoric acid is increased through the use of either water or alcohol. The water or alcohol provides a solvent to assist in the through mixing of the salt of hydrofluoric acid with the keratin.

The composition so formed is useful for pharmaceutical treatments, topical cleansers, soaps, creams, and as additives to a variety of cosmetics.

In the preferred embodiment, by weight, the metallic salt of hydrofluoric acid constitutes less than twenty percent of the keratin/hydrofluoric acid salt combination. The actual relative amounts are chosen to obtain the desired results for the contemplated application. Such applications include topical cosmetics, creams, soaps, and additives for pharmaceuticals.

As those of ordinary skill in the art recognize, a soap is a type of detergent in which the water-solubilizing group is a carboxylate, COO—, and the positive ion is usually sodium or potassium.

In the case of some creams, the cream, containing both keratin and the salt of hydrofluoric acid, is applied to the user's epidermal and then left to have it curative affect.

The invention, using a salt of hydrofluoric acid within a topically applied medium, significantly increases the permeability of the user's skin so that the active ingredient is more effective.

The invention, together with various embodiments thereof, will be more fully explained by the accompanying drawings and the following description.

DRAWINGS IN BRIEF

DRAWINGS IN DETAIL

Figure 1A:
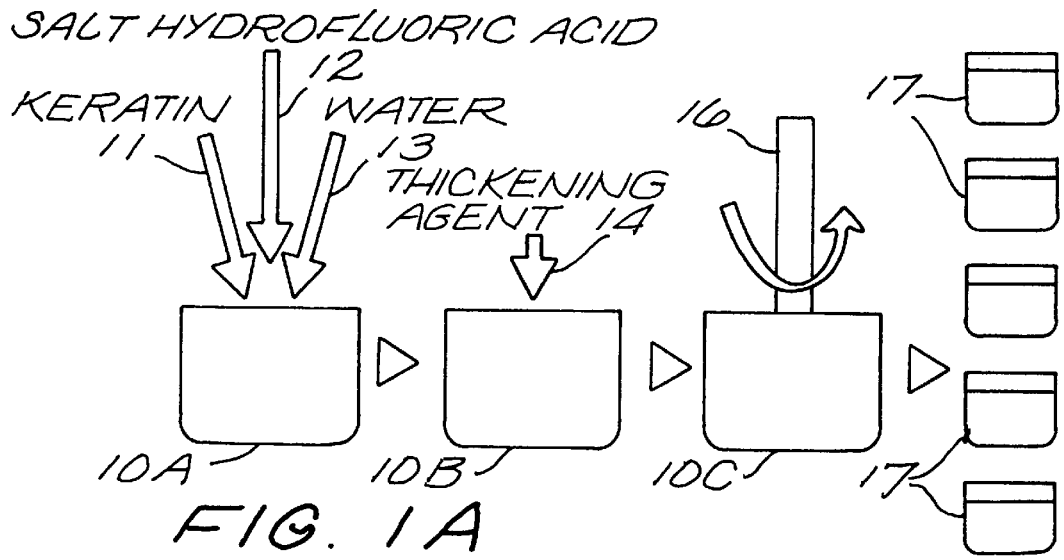
FIGS. 1A and 1B illustrate the steps taken in the production of the mixture for two embodiments of the invention.
Figure 1B:
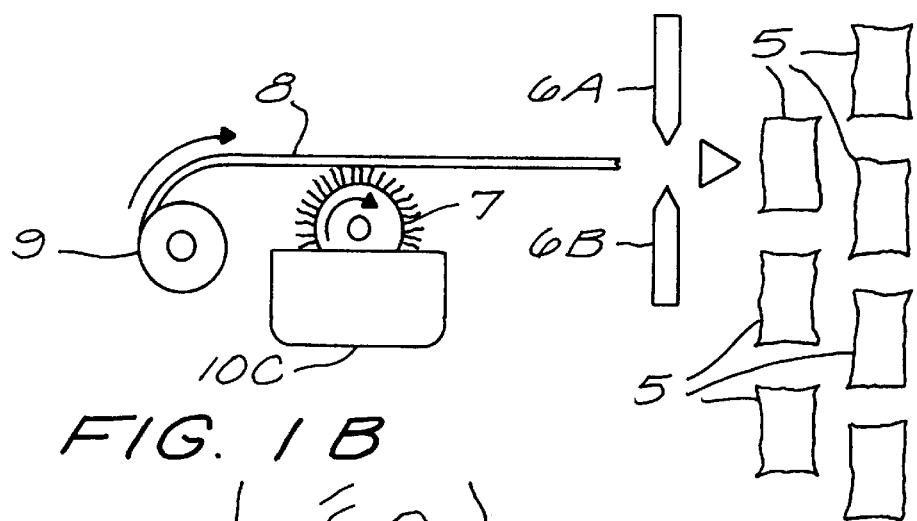

FIGS. 1A and 1B illustrate the steps taken in the production of the mixture for two embodiments of the invention.

Referring to FIG. 1A, into container 10A is placed the keratin 11, the salt of hydrofluoric acid 12, and a quantity of water 13. This mixture is the suspended through the use of a thickening agent 14 (i.e. carboxyl or a gelatin). Container 10B is then mixed 16 to form a uniform blending of the mixture.

The combination so formed, in container 10C, is then packaged 17 in small bottles for distribution to consumers.

The mixture is distributed in a different manner for the production process shown in FIG. 1B. The mixture from container 10C is applied to substrate 8 using roller 7 as substrate 8 is pulled from source roller 9.

The substrate/mixture combination is then cut by blades 6A and 6B and packaged in single use packages 5.

Figure 2:
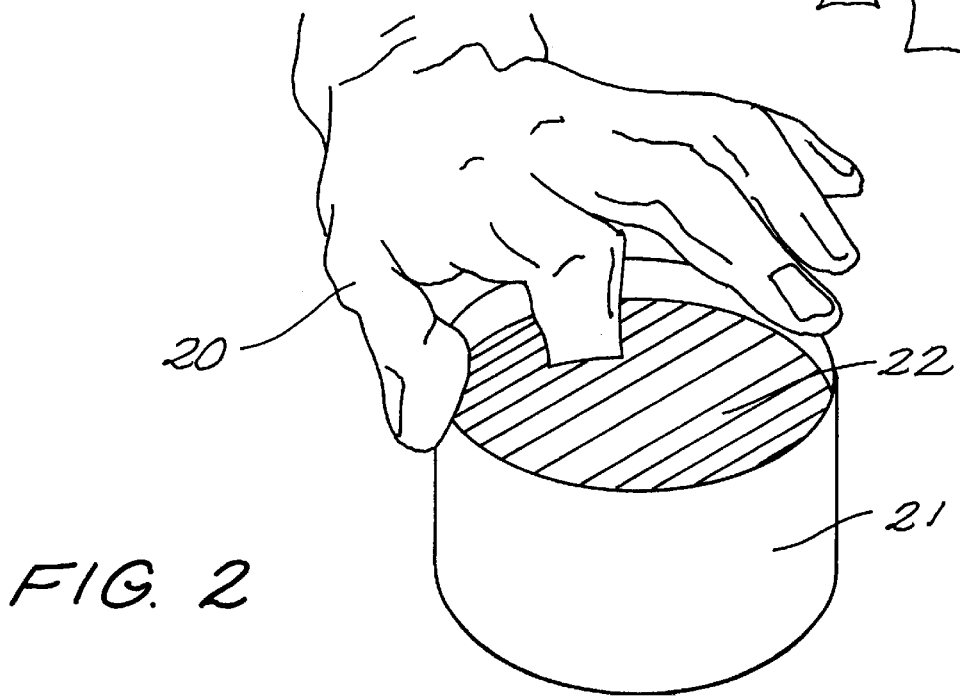
FIG. 2 illustrates an embodiment of the invention used for the treatment of nails as used in a soak arrangement.

FIG. 2 illustrates an embodiment of the invention used for the treatment of nails as used in a soak arrangement.

As illustrated, user 20 places a finger in dispenser 21 which contains a mixture 22 of keratin and salt of fluoric acid. The soaking arrangement, due to the enhanced solubility of the keratin caused by the salt of fluoric acid, readily penetrates the finger nails of user 20 so that the nails are properly treated by the keratin.

Figure 3:
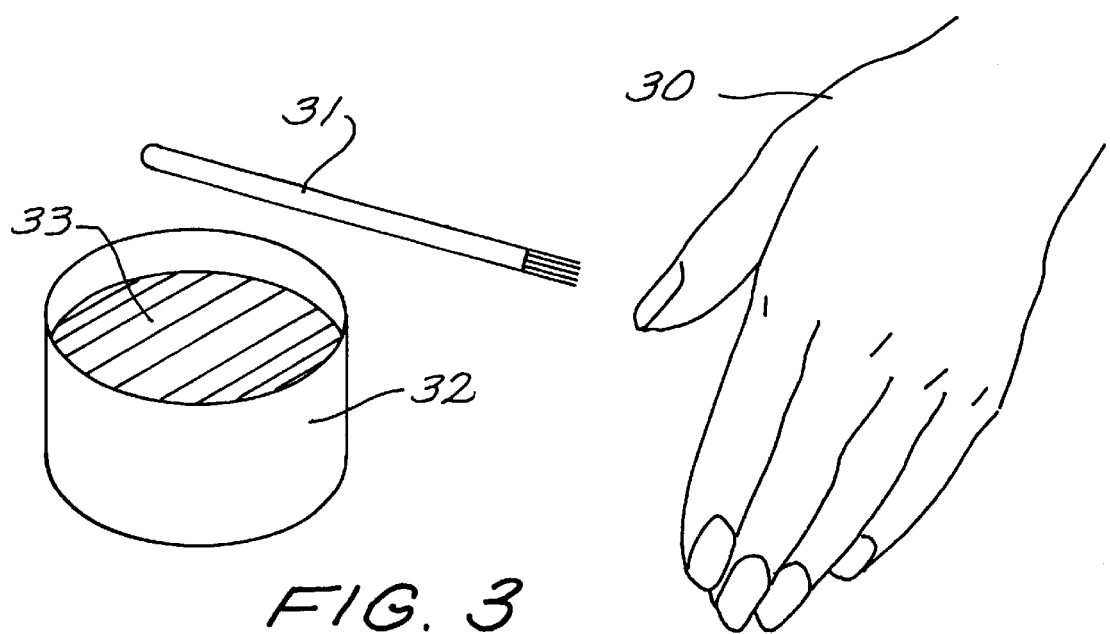
FIG. 3 illustrates an embodiment of the invention which is applied to the nails using a brush.

FIG. 3 illustrates an embodiment of the invention which is applied to the nails using a brush.

As discussed relative to FIG. 2, the combination of keratin and salt of fluoric acid is highly permeable and is beneficial for the treatment of nails and hair. In FIG. 3, application of the keratin/fluoric acid combination 33, is accomplished by using brush 31 to apply the mixture from container 32 onto the nails of user 30.

In another embodiment of the invention, the keratin/ fluoric acid mixture is combined with a soap allowing the mixture to be applied directly onto the user's hair for the strengthening of the hair.

Figure 4:
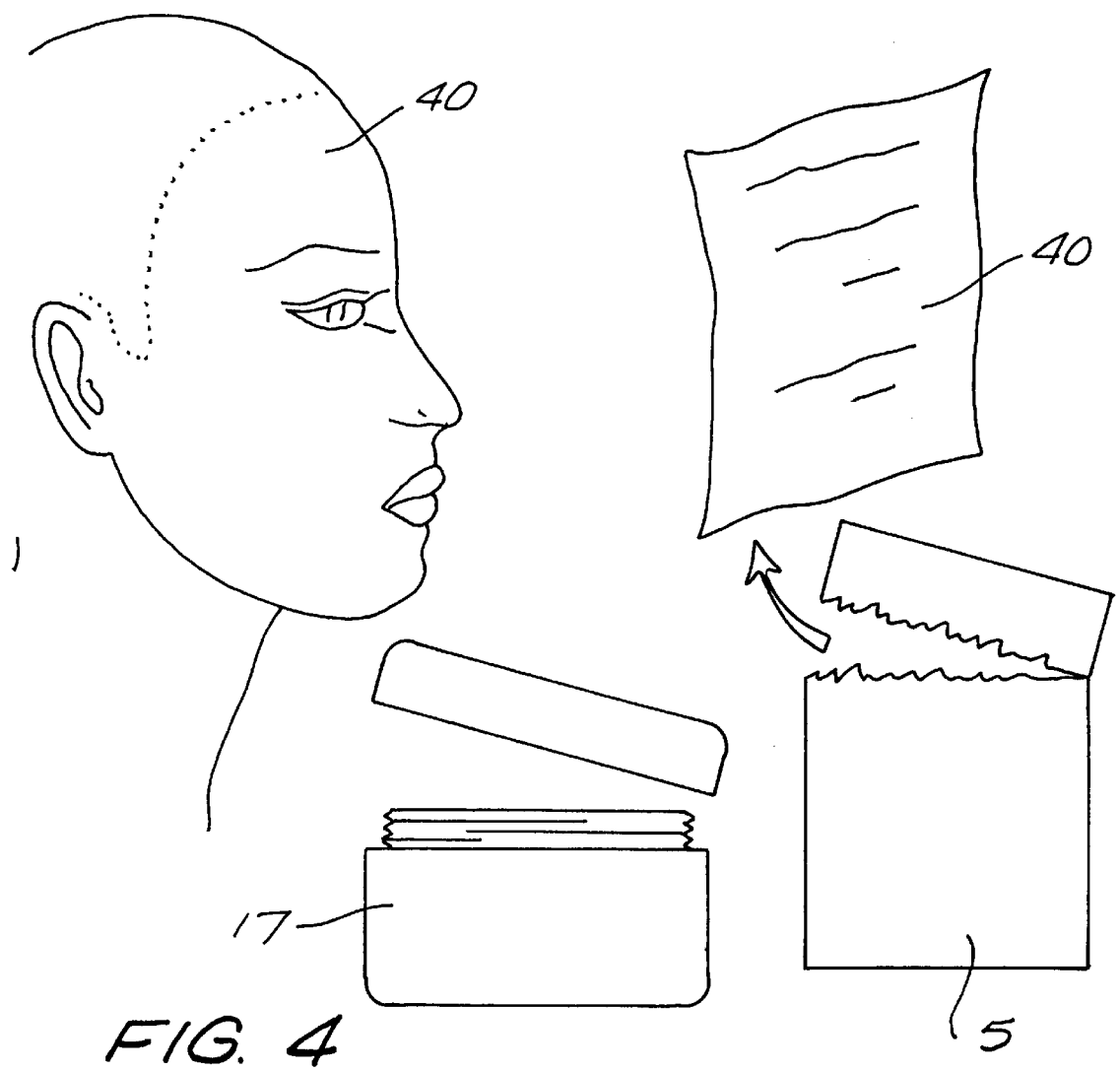
FIG. 4 illustrates two embodiments of the invention being used as a cosmetic.

FIG. 4 illustrates two embodiments of the invention being used as a cosmetic.

In this illustration, user 40 is able to apply the cosmetic from bottle 17 directly onto her face. This external topical application of the mixture of keratin/salt of fluoric acid has great therapeutic affects as the keratin has been rendered highly soluble due to the salt of fluoric acid.

As an alternative, user 40 is able to open package 5 and withdraw a single use sheet 40 which has the mixture of keratin/salt of fluoric acid thereon.

It is clear that the present invention creates a highly improved soluble and permeable mixture for the use in a wide variety of applications from cosmetics to nail treatment.

What is claimed is:

1. A composition for external topical treatment of skin conditions comprising, in a carrier, cosmetically active ingredient, a metallic salt of hydrofluoric acid, and keratin.

2. The composition according to claim 1, further including a solvent.

3. The composition according to claim 1 wherein said solvent includes water.

4. The composition according to claim 2, wherein said solvent includes alcohol.

5. The composition for the topical treatment of skin according to claim 2, further including a gelatin forming substance.

6. The composition according to claim 5, wherein said gelatin forming substance includes carboxyl.

7. The composition according to claim 1, wherein, by weight, said metallic salt of hydrofluoric acid is substantially less than said keratin within said carrier.

8. The composition according to claim 7, wherein, by weight, said metallic salt of hydrofluoric acid is less than twenty percent of the keratin.

9. A cosmetic comprising, in a cream base, a mixture of keratin and a salt of hydrofluoric acid.

10. The cosmetic according to claim 9, further including a flexible substrate and wherein a layer of said mixture is formed on a surface of said flexible substrate.

11. The cosmetic according to claim 9, further including a soap.

12. The cosmetic according to claim 9, further including water mixed with said salt of hydrofluoric acid.

13. The cosmetic according to claim 9, further including an alcohol mixed with said salt of hydrofluoric acid.

14. A cosmetic adapted to be applied to the skin of a user and left thereon, said cosmetic comprising:
 a) a softening agent having keratin therein;
 b) a salt of hydrofluoric acid; and
 c) a gelatin forming substance.

15. The cosmetic according to claim 14, further including a container for holding said cosmetic, said container adapted to permit a user's finger to be inserted into said cosmetic.

16. The cosmetic according to claim 14, further including:
 a) a flexible substrate having said cosmetic secured to a surface thereon; and
 b) a packaging enclosing said flexible substrate.

17. An additive for cosmetics comprising:
 a) a first quantity of keratin; and
 b) a second quantity of salt of hydrofluoric acid.

18. The additive according to claim 17, wherein, by weight, said first quantity is substantially greater than said second quantity.

19. The additive according to claim 18, wherein said second quantity constitutes, by weight, less than twenty percent of said second quantity.

20. The additive according to claim 17, further including a gelatin adapted to suspend said first quantity of keratin and the second quantity of salt of hydrofluoric acid.

21. A method of topically treating skin conditions comprising the step of contacting a user's skin layer with a carrier having an cosmetically active ingredient and a metallic salt of hydrofluoric acid.

22. The method of topically treating skin according to claim 21 further including the step of applying water to the user's skin layer after the step of contacting with a carrier.

* * * * *